(12) United States Patent
Hamel et al.

(10) Patent No.: US 10,912,889 B2
(45) Date of Patent: Feb. 9, 2021

(54) AUTO-INJECTOR

(71) Applicant: Duoject Medical Systems Inc., Bromont (CA)

(72) Inventors: Simon Hamel, Knowlton (CA); Sylvain Cloutier, Magog (CA); Yan Tremblay, Orford (CA); Mathieu Viens, Granby (CA)

(73) Assignee: Duoject Medical Systems Inc., Bromont (CA)

( * ) Notice: Subject to any disclaimer, the term of this patent is extended or adjusted under 35 U.S.C. 154(b) by 161 days.

(21) Appl. No.: 16/501,159

(22) PCT Filed: Aug. 25, 2017

(86) PCT No.: PCT/CA2017/000197
§ 371 (c)(1),
(2) Date: Feb. 27, 2019

(87) PCT Pub. No.: WO2018/039769
PCT Pub. Date: Mar. 8, 2018

(65) Prior Publication Data
US 2019/0192777 A1 Jun. 27, 2019

(30) Foreign Application Priority Data
Aug. 29, 2016 (CA) ..................... 2940544

(51) Int. Cl.
*A61M 5/20* (2006.01)
*A61M 5/24* (2006.01)
(Continued)

(52) U.S. Cl.
CPC ........ *A61M 5/2033* (2013.01); *A61M 5/2455* (2013.01); *A61M 5/31576* (2013.01); *A61M 5/326* (2013.01); *A61M 2005/206* (2013.01)

(58) Field of Classification Search
CPC .............. A61M 5/2033; A61M 5/2455; A61M 5/31576; A61M 5/326; A61M 2005/206
(Continued)

(56) References Cited

U.S. PATENT DOCUMENTS

2002/0183690 A1* 12/2002 Arnisolle ............ A61M 5/2066
604/83
2006/0229570 A1* 10/2006 Lovell ............... A61M 5/31551
604/218

* cited by examiner

*Primary Examiner* — Phillip A Gray
(74) *Attorney, Agent, or Firm* — Eric Fincham

(57) ABSTRACT

A auto-injector device having a housing (212, 214), a cartridge for containing a medicament, a first needle tip (230) arranged to penetrate said cartridge, a second needle tip (230) for injecting said medicament into a target, said first and second needle tips being in fluid communication, a plunger rod (242) to move said cartridge so as to be pierced by said first needle tip, said plunger rod (242) having a recess (270) in an end thereof, the improvement comprising a battery (258), a printed circuit board (250) electrically communicating with said battery, an electrically conductive element (274) having a first end in electric communication with said battery (258) and printed circuit board (250), a second end within said recess (270) in said plunger rod (242), said second end being electrically insulated, a coil spring (246) surrounding said electrically conductive element and being spaced therefrom, the arrangement being such that when said plunger rod (242) is activated, said second end of said electrically conductive element is released from said recess (270) in said plunger rod (242) and contacts said coil spring (246) to complete an electric circuit.

4 Claims, 27 Drawing Sheets

(51) Int. Cl.
*A61M 5/315* (2006.01)
*A61M 5/32* (2006.01)
(58) Field of Classification Search
USPC .......................................................... 604/135
See application file for complete search history.

AUTO-INJECTOR

FIELD OF THE INVENTION

The present invention relates to a medical device and more particularly, relates to a medical delivery device known as an auto-injector for injecting a medicament into the body of a patient.

BACKGROUND OF THE INVENTION

Auto-injectors are well known in the art and, as aforementioned, are used to inject a medicament into the body of a patient. The injection is usually done by the patient. Typically, the auto-injectors are used for allergic reactions such as exposure to peanuts, shellfish, certain drugs, toxins and the like, all of which can result in an allergic reaction in some individuals. Typically, the allergic reaction will lead to anaphylactic shock which results in a sharp drop in blood pressure. Other reactions such as airway constriction can also occur.

In order to respond to such a reaction, the individual may carry an auto-injector to administer an injection of a substance which will provide relief from the allergic reaction. Typically such an injection is of adrenaline. As aforementioned, auto-injectors are known in the art and come in many different configurations. Typically, the user is supposed to place a first end against a body surface such as a thigh and then a trigger is activated to commence the injection process. However, since the user is already suffering from the allergic reaction, confusion can result. Typically, the user may put the wrong end against the thigh and as a result, the auto-injector can be activated. Naturally, this can result in problems since the user usually only carries a single dose auto-injector and unless other sources are available, the allergic reaction will not be treated.

SUMMARY OF THE INVENTION

It is an object of the present invention to provide for an auto-injector which will result in a consistent and reliable activation of the auto-injector.

It is a further object of the present invention to provide an auto-injector which will signal that an injection has been administered.

The auto-injector has an outer housing with a proximal end and a distal end, an inner housing, a cartridge located within the inner housing. The cartridge contains a medicament and has one end sealed by a pierceable member. There is also provided a needle hub, the needle hub having first and second piercing tips which are in fluid communication. There is an actuating assembly which is arranged to move an actuator from a first storage position to an activated position wherein the first piercing tip extends outwardly of the outer housing of the proximal end and the second piercing tip pierces the pierceable member. The arrangement also includes a first trigger located at the distal end, the trigger being operative to cause activation of the actuating assembly and a second trigger located at the proximal end, the arrangement being such that the second trigger must be activated to permit activation of the first trigger.

Preferably, the outer housing is formed of two pieces which are secured to each other by any suitable means such as clips, and fastening devices such as screws, etc. The cartridge can be selected from those known in the art and is usually in the form of an elongated vessel containing a medicament. The medicament is contained within the cartridge by having at least one end thereof sealed by a pierceable member. The pierceable member may comprise the cap of the cartridge or alternatively, could comprise a plunger sealing the internal cavity. Generally, it is preferred that the cap be the one provided with the pierceable member.

The needle comprises a staked-in needle with first and second piercing tips as is known in the art. The first and second piercing tips are in fluid communication so that the medicament can flow from the cartridge to the injection site.

The actuating assembly includes upper and lower members. The terms "upper" and "lower" are relative and in the instant application, the word upper refers to the part of the actuating assembly closest to the distal end of the auto-injector. Inversely, the term lower refers to that portion of the actuating assembly which is closest to the proximal end of the auto-injector.

The actuating assembly secures the upper and lower portions together with compressed springs being mounted therebetween. A trigger mounted at the distal end is designed to release the lower member from the upper member. The springs act to drive the lower portion with a force sufficient to cause the needle to extend outwardly of the outer housing and the cartridge to be pierced by the needle.

A first trigger is located at the distal end and a second trigger is located at the proximal end. The arrangement is such that only upon activation of the second trigger by the patient or user pressing the auto-injector against the site to be injected will cause the actuating assembly to move to a position where it can be actuated by the first trigger. Following use of the device, the needle hub will be returned to a position by means of a spring such that the needle no longer projects outwardly of the outer housing and thus is safe to handle.

The auto-injector is preferably provided with a printed circuit board and battery. Many different options can be built into the printed circuit board. Thus, one of the major problems with auto-injectors is the patient requiring use of the same may tend to forget to carry the auto-injector at all times. In order to overcome this, the auto-injector could be electronically linked to a cell phone of the user. Once a certain distance exists between the telephone and the auto-injector, a reminder is given to the user that the auto-injector is not present. The reminder may be any suitable including auditory or visual.

Other features could include an arrangement that once it has been activated, it will notify one or more sites that it has been used. This can be used, in conjunction with GPS capabilities to locate the use and ensure that the patient is not in distress. For example, the device could have the capability of sending a message to a close relative or a Doctor or other medical centre advising that it has been used.

The device could also be used to monitor the exposure of the device to ambient conditions. This can be important with certain medications which are sensitive to heat. If the device is exposed to sufficient heat for a certain of time, a message could be sent advising that the medication may have been comprised. This could be used to automatically forward a replacement device to the user.

Similarly, the device could also be programmed to automatically reorder when the expiration date is reached.

Still further, if for some reason, a second injection is required, the capability of locating other similar devices in the immediate area could be programmed into the device.

The arrangement of signalling that the device has been used could be easily built into the device. Thus, two metallic contacts could be in a normally separated position prior to activation. Once the actuating assembly has been moved, this could permit the two electrical contacts to contact each other and thereby send a signal.

The auto-injector of the present invention has an arrangement wherein the plunger rod (part of the actuator) includes an internal recess. The internal recess is utilized to keep an electrically conductive member in an electrically insulated location prior to activation. However, following activation, the end of said electrically conductive member is allowed to make contact with an electrical contact to thereby complete an electric circuit and cause the same to function as desired.

BRIEF DESCRIPTION OF THE DRAWINGS

Having thus generally described the invention, reference will be made to the accompanying drawings illustrating an embodiment thereof, in which.

DETAILED DESCRIPTION OF THE INVENTION

Figure 1:
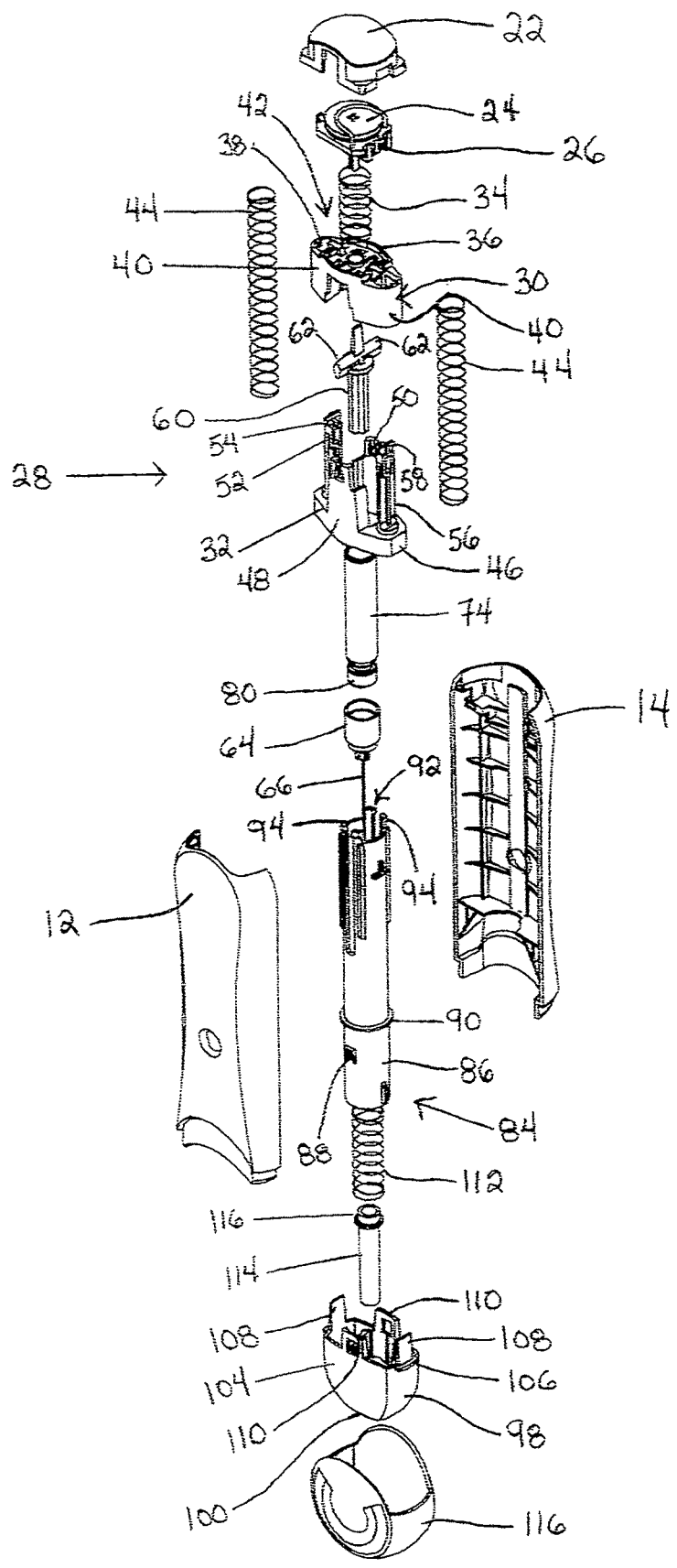
FIG. 1 is an exploded view of an auto-injector of the present invention.
Figure 2:
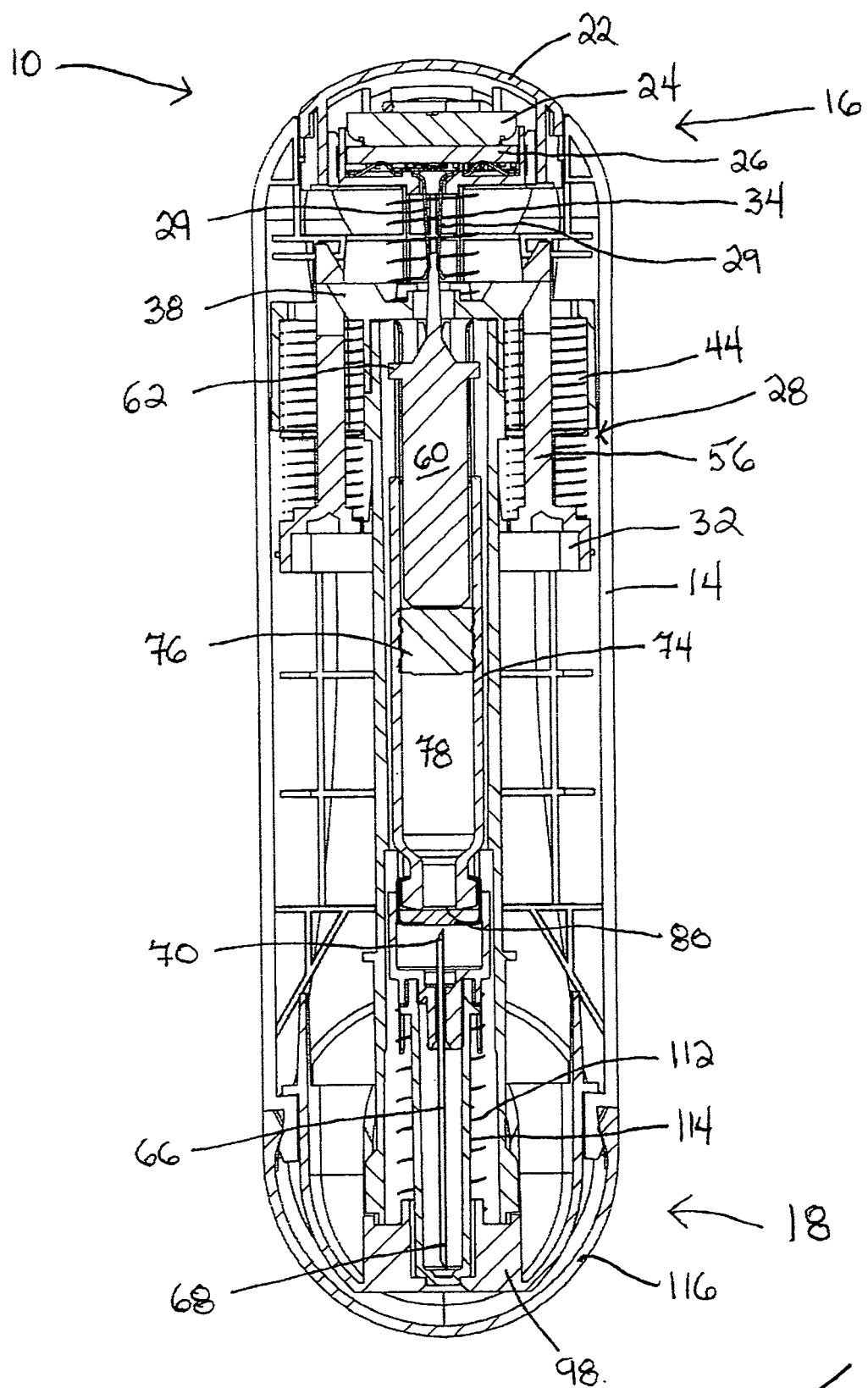
FIG. 2 is a sectional view of the auto-injector when in a stored position.
Figure 3:
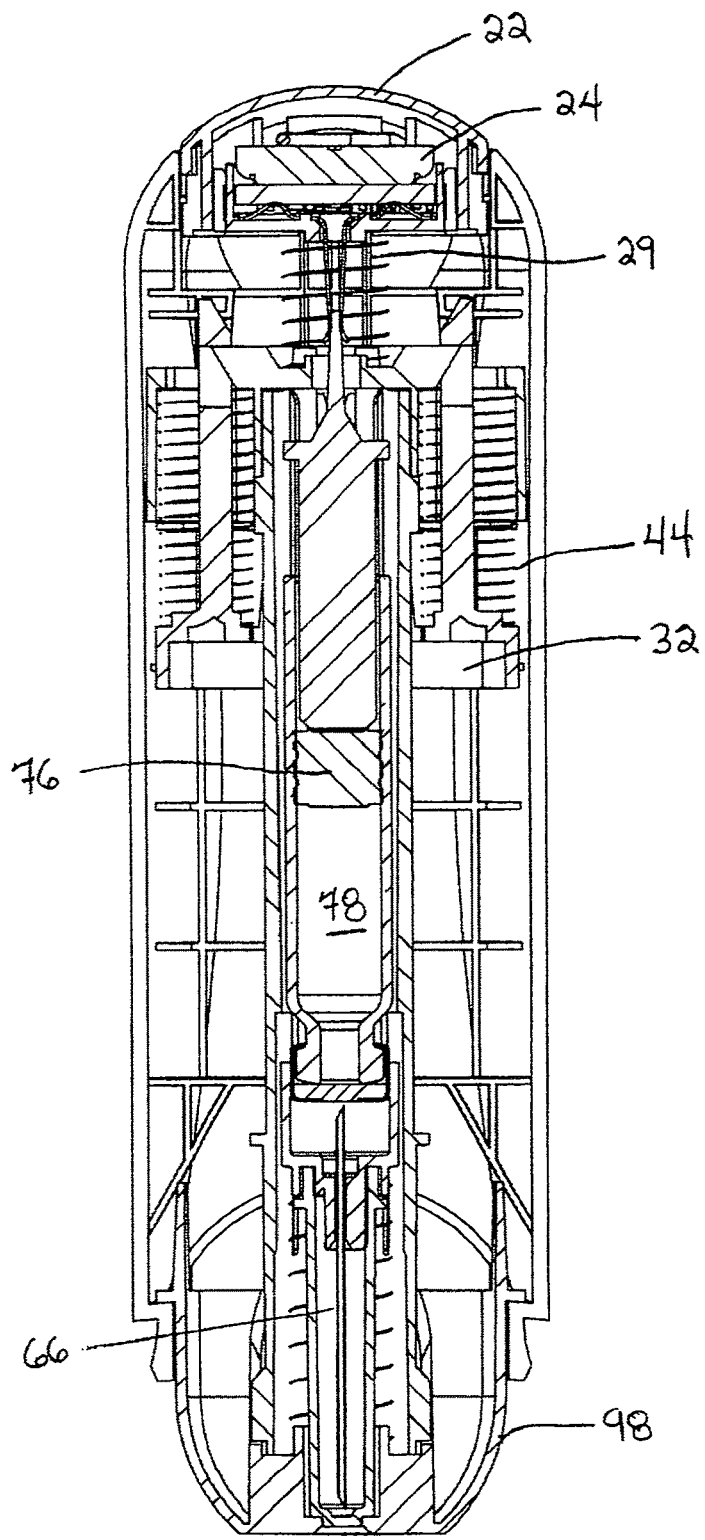
FIG. 3 is a sectional view illustrating removal of the cap.

Referring to the drawings in greater detail and by reference characters thereto, there is illustrated an auto-injector generally designated by reference numeral 10. Auto-injector 10 is designed to inject or administer an injection of a substance.

Auto-injector 10 has an outer housing characterized by a first half outer housing 12 and a second half outer housing 14. For the purposes of this disclosure, Applicant will refer to a distal end generally designated by reference numeral 16 and a proximal end generally designated by reference numeral 18. As used herein, the term "distal end" refers to the end remote from the injection site while the term "proximal end" refers to the end closest to the injection site.

At distal end 16, there is provided a trigger 22 in the form of a push button. Mounted immediately below trigger 22 is a battery 24 and a printed circuit board 26. Printed circuit board 26 is used to control the electronic functions of the device as will discussed hereinbelow. A spring 34 biases said trigger 22. A pair of metallic contacts 29 extend downwardly from printed circuit board 26. They are separated prior to activation.

Auto-injector 10 includes an actuating assembly generally designated by reference numeral 28. Actuating assembly 28 includes an upper member generally designated by reference numeral 30 and a lower member generally designated by reference numeral 32.

Upper member 30 has a recessed top surface 36 having a plurality of apertures 38 formed therein. There are four such apertures 38. On either side, there are provided a pair of ears 40 each having a passageway generally designated by reference numeral 42 extending therethrough.

Lower member 32 includes a base 46 with a pair of upwardly extending side walls 48, 50. On a first side, there is provided a pair of legs 52 which are slightly spaced apart and have tabs 54 at an upper end thereof. Similarly, there are provided legs 56 on the opposite side with each having tabs 58 formed thereon. A pair of compressed springs 44 extend about legs 52, 56 between lower member 32 and upper member 30. A recess 31 is provided at the upper edge.

Situated between upper member 30 and lower member 32 is a movable plunger rod 60 having diamond shaped protrusions 62 on either thereof. Protrusions 62 fit within recess 31.

A needle hub 64 has a staked-in needle 66 with a first piercing tip 68 and a second piercing tip 70. A cartridge 74 contains a medicament 76. Cartridge 74 has a plunger 78 within its body and a pierceable top 80.

Auto-injector 10 has an inner housing 84. Inner housing 84 has a cylindrical base 86 with protrusions 88 located thereon. Above protrusions 88, there is provided a circular stopper flange 90. The upper portion of inner housing 84 includes slots 92 to thereby divide the inner housing 84 into leg-like structures. At the upper portion of inner housing 84, there are provided tabs 94 which are designed to engage with top surface 36 of upper member 30 to thereby retain inner housing 84 in position.

At its proximal end 18, auto-injector 10 is provided with a trigger 98. Trigger 98 has a bottom wall 100 with an aperture 102 formed therein to permit staked-in needle 68 to extend outwardly therefrom. Trigger 98 also has a front wall 104 and a back wall 106. Tabs 108 extend upwardly therefrom. There are also provided inverted U-shaped members 110 which are designed to engage with protrusions 88 of inner housing 84 to thereby interconnect the two members. A housing 114 has a flange 116 with a coil spring 112 which extends between trigger 98 and needle hub 64 over housing 114.

A cover 116 is designed to extend about trigger 98. Cover 116 is removable when use of auto-injector 10 is required.

Figure 4:
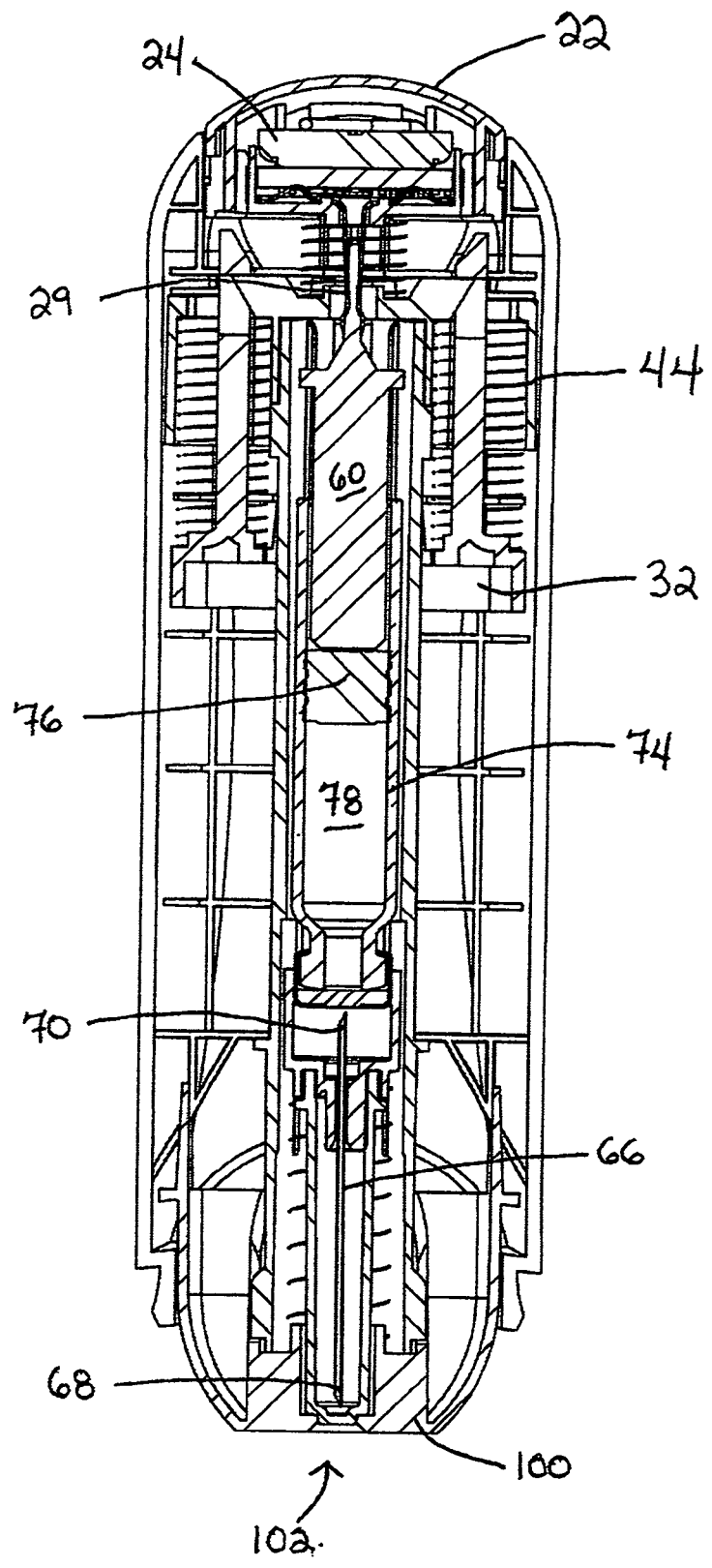
FIG. 4 is a sectional view illustrating commencement of the pressing of the second trigger.
Figure 5:
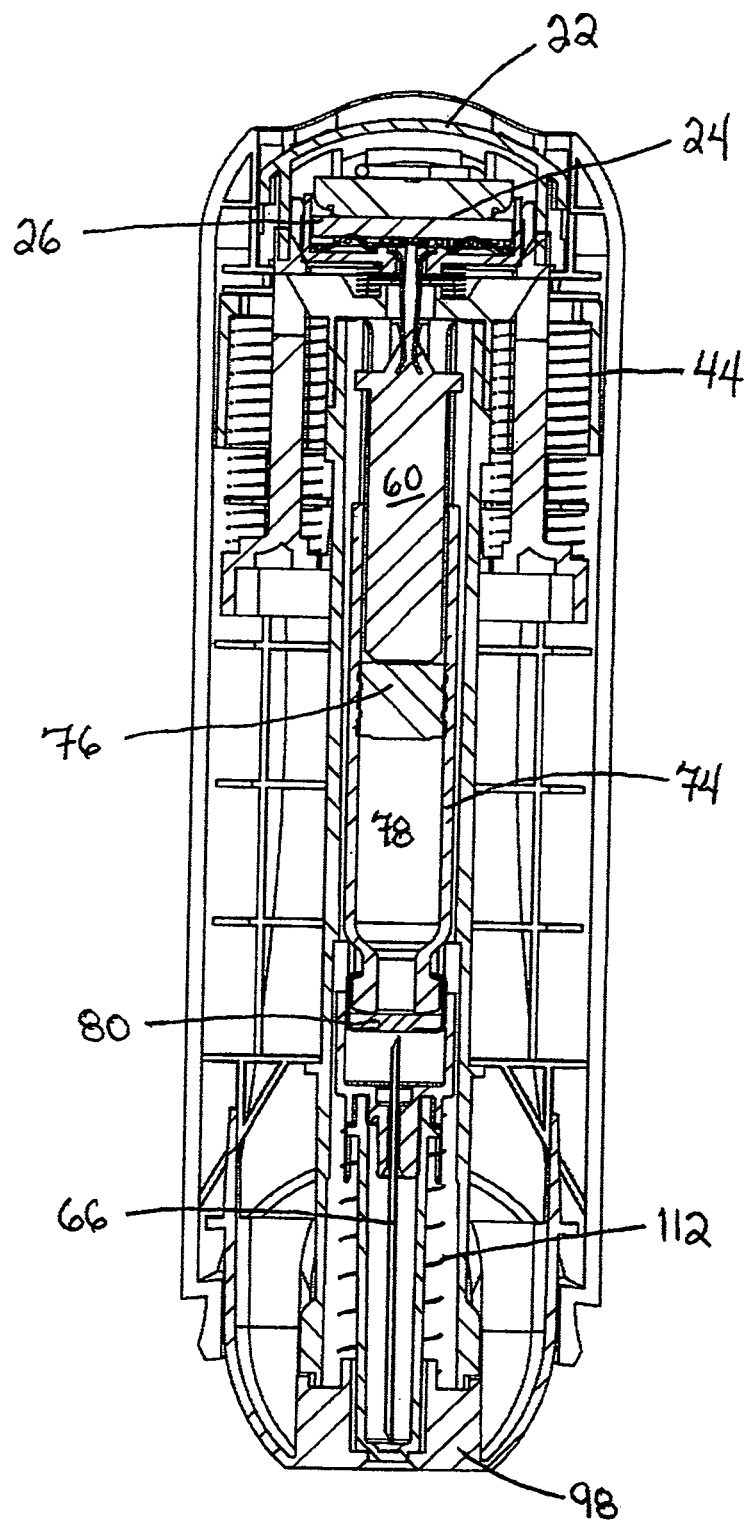
FIG. 5 is a sectional view illustrating commencement of the activation of the first trigger.
Figure 6:
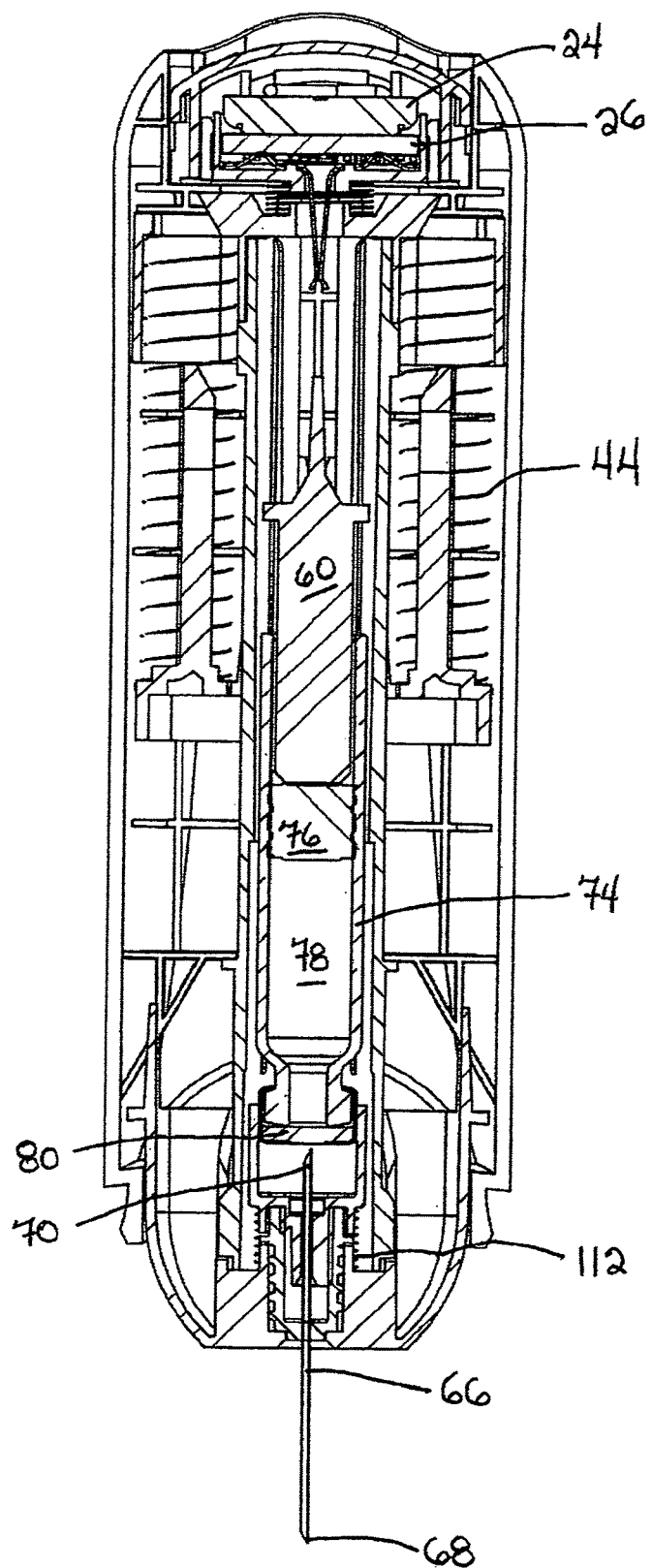
FIG. 6 is a sectional view illustrating the auto-injector during activation.
Figure 7:
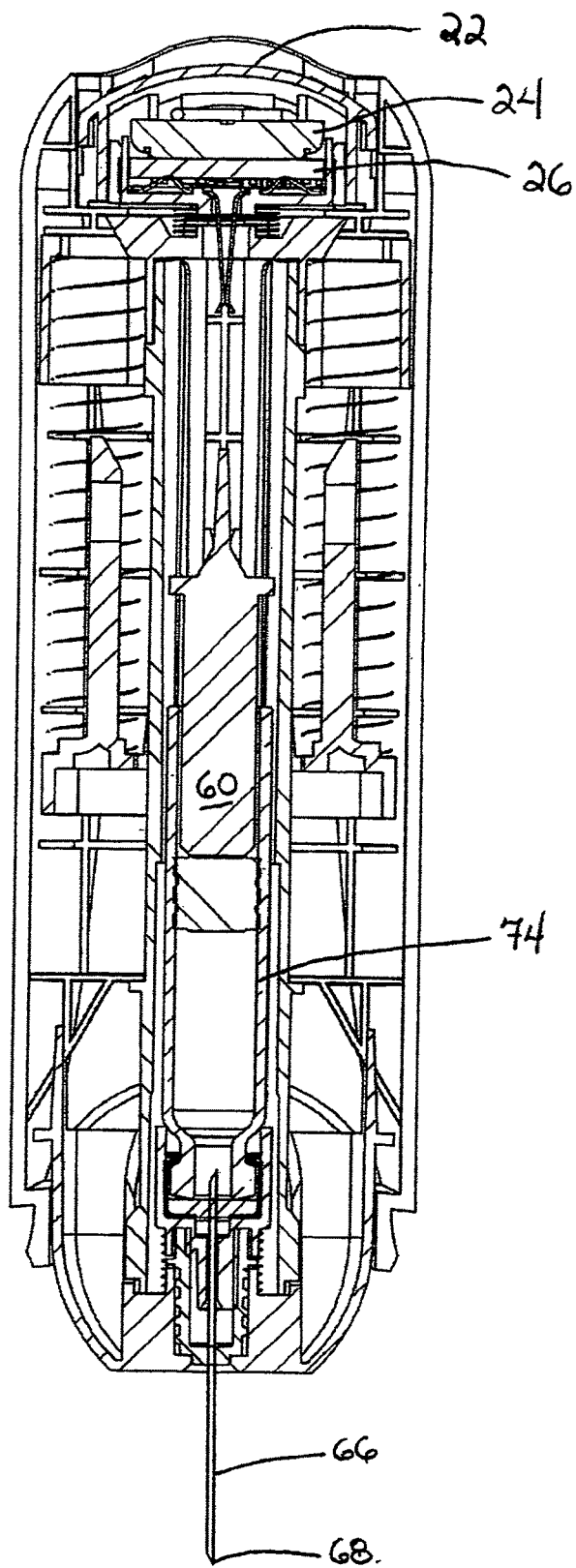
FIG. 7 is a sectional view illustrating the auto-injector fully activated.
Figure 8:
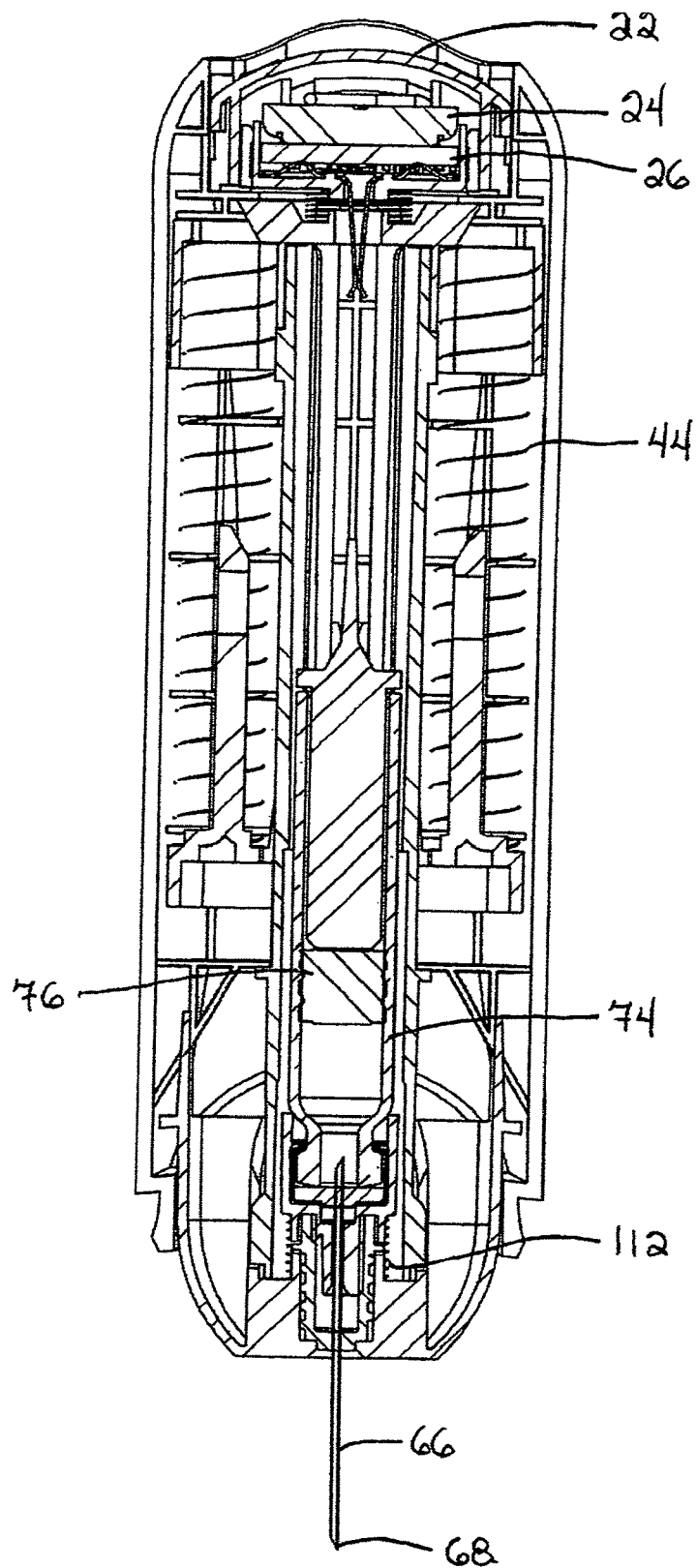
FIG. 8 is a sectional view illustrating the auto-injector at the end of activation.
Figure 9:
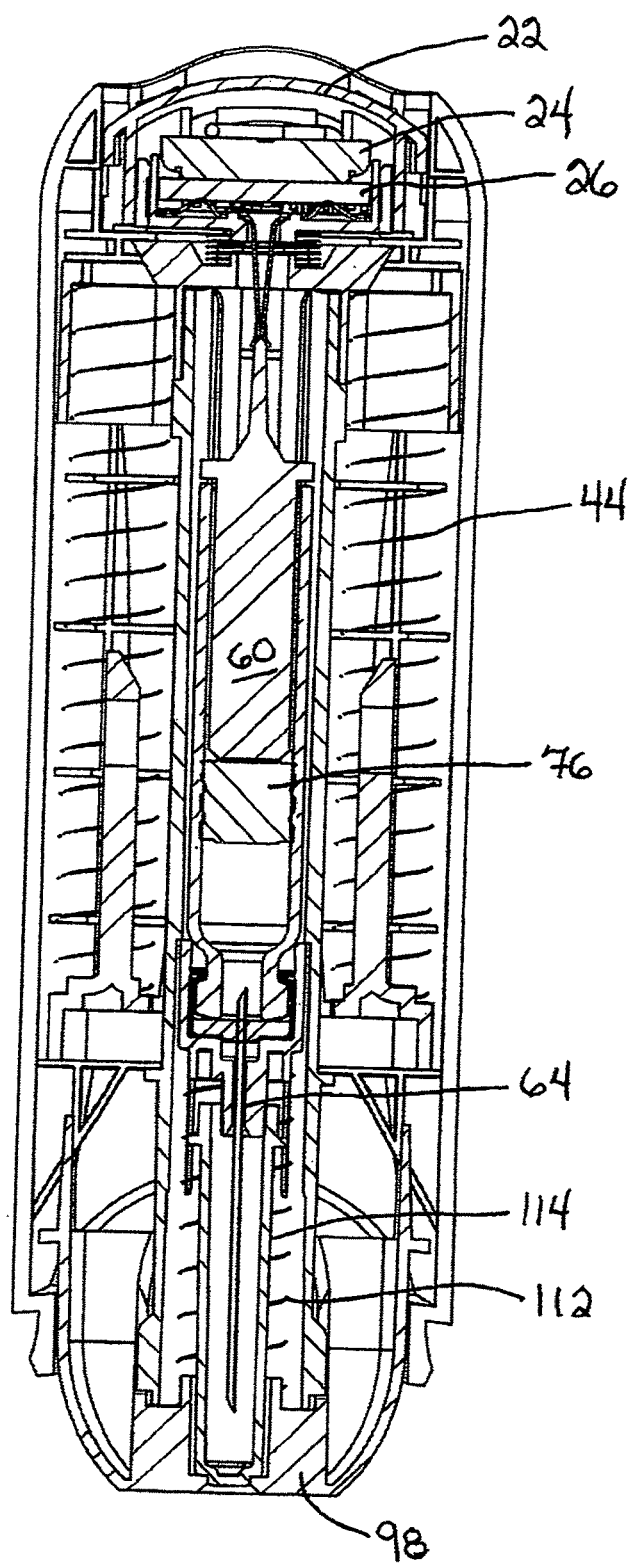
FIG. 9 is a sectional view illustrating retraction of the needle.
Figure 10:
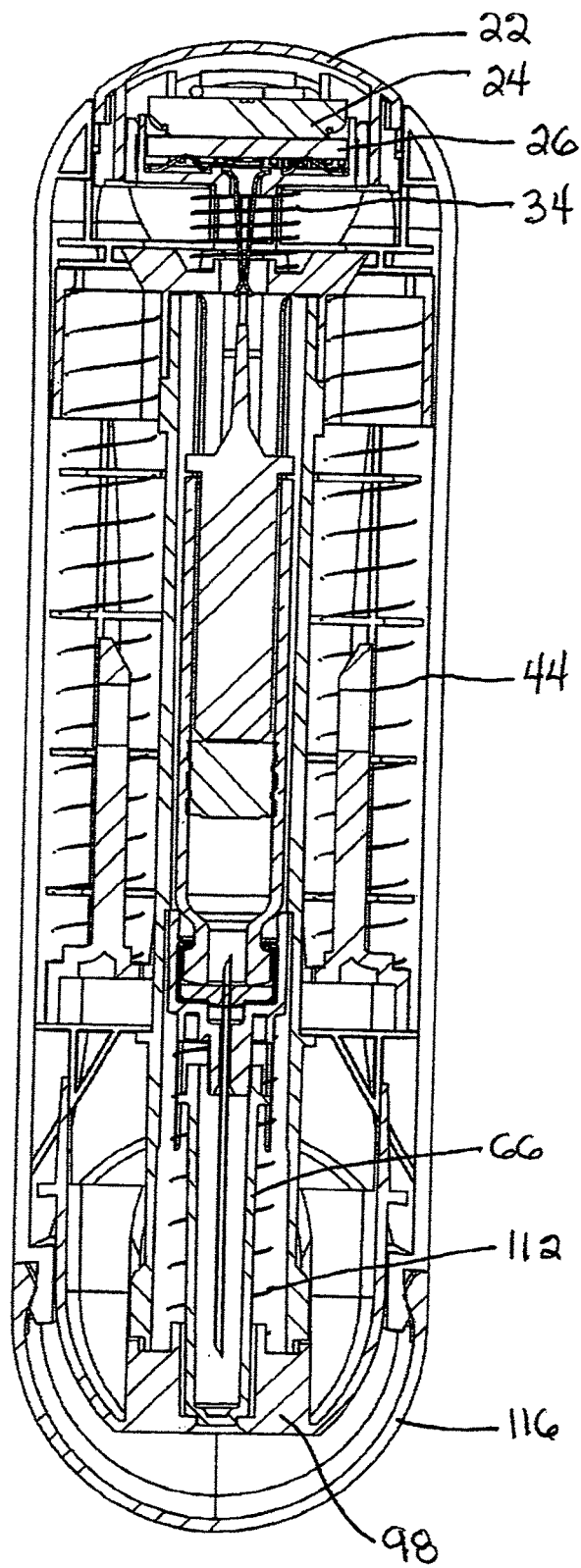
FIG. 10 is a sectional view illustrating the spent auto-injector with the cover replaced.
Figure 11:
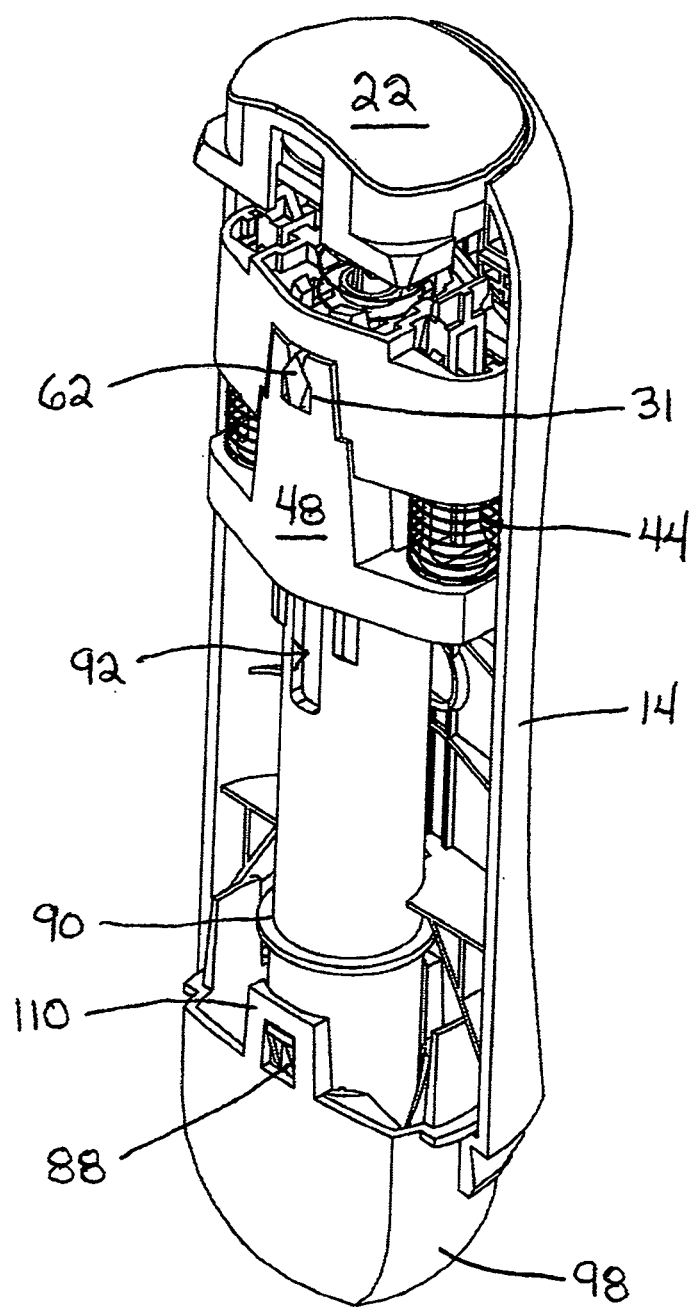
FIG. 11 is a perspective cutaway view of the auto-injector when in the position shown in FIG. 3.
Figure 12:
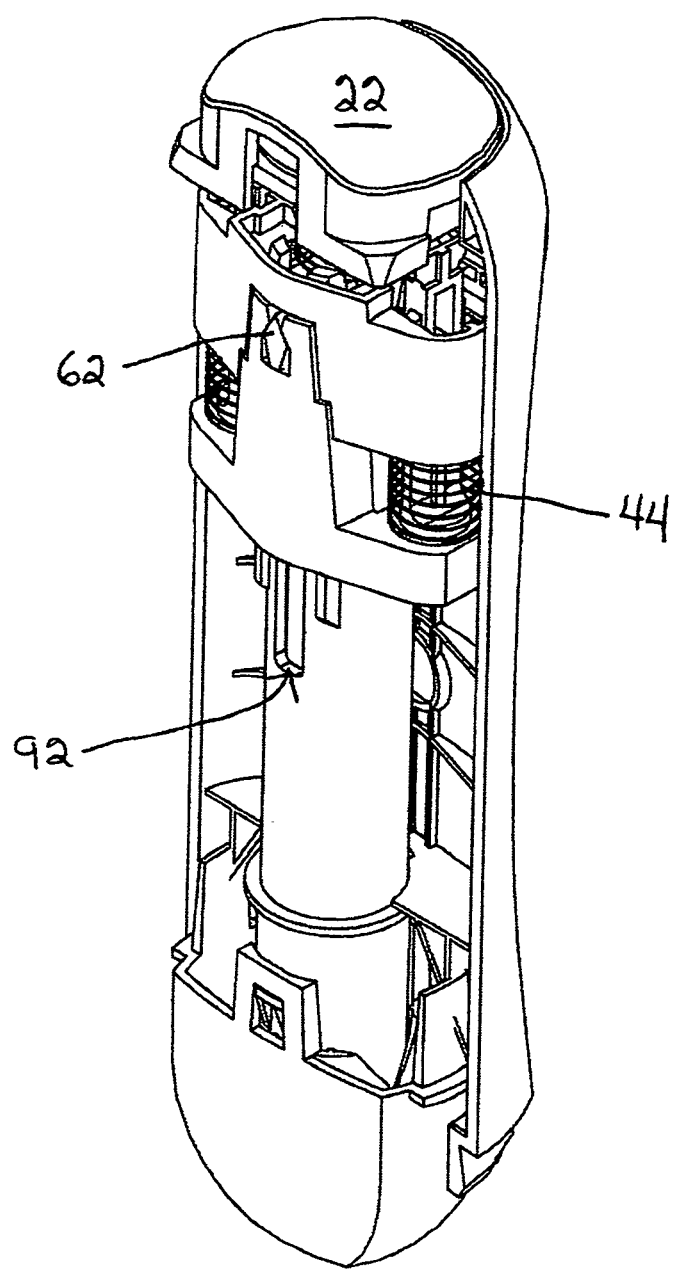
FIG. 12 is a perspective cutaway view of the auto-injector in the position illustrated in FIG. 4.
Figure 13:
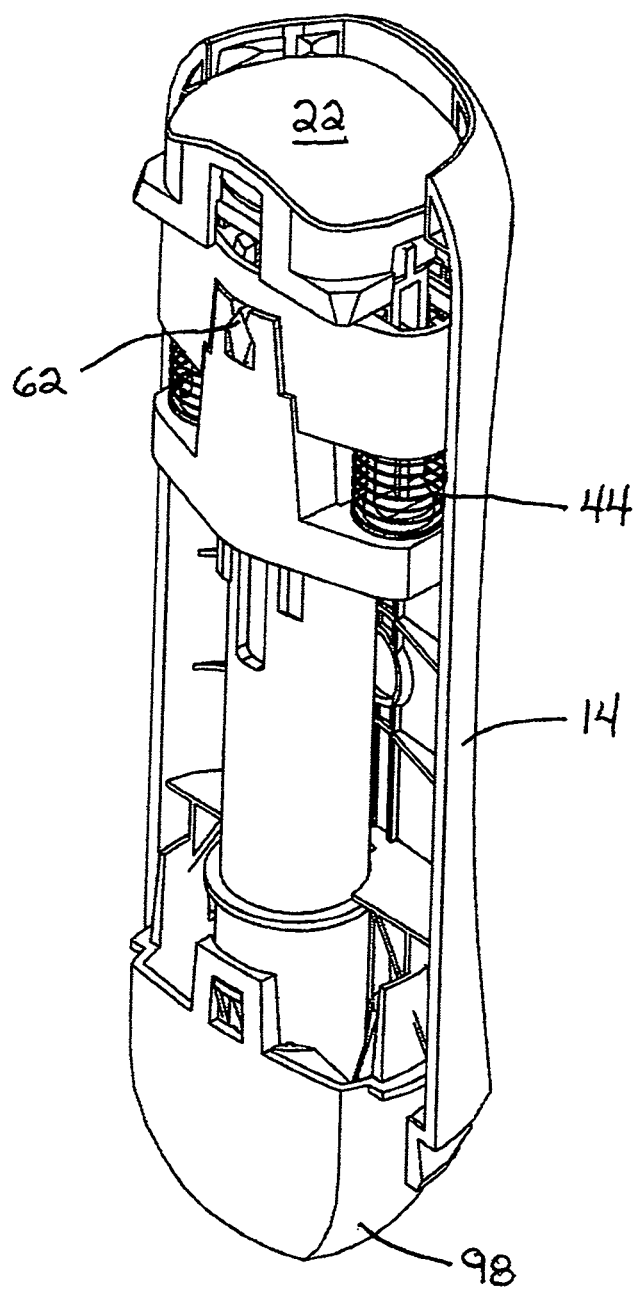
FIG. 13 is a perspective cutaway view of the auto-injector in the position illustrated in FIG. 5.
Figure 14:
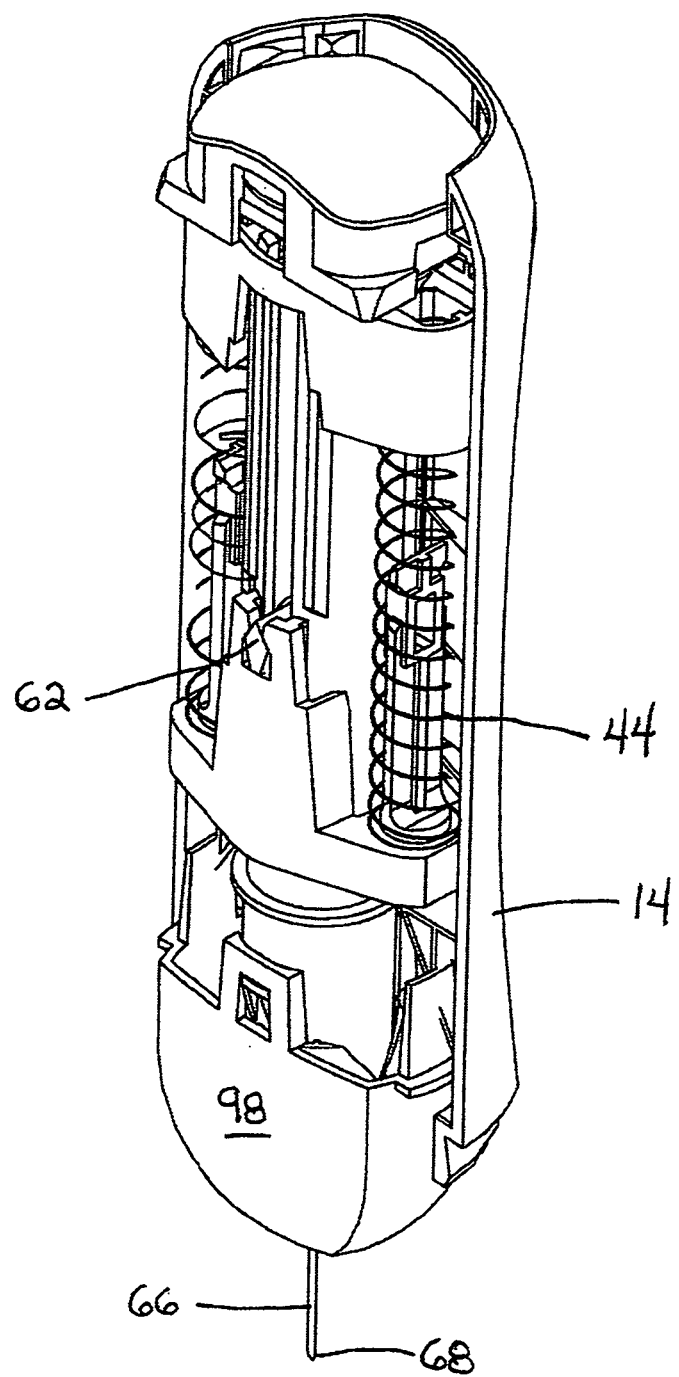
FIG. 14 is a perspective cutaway view of the auto-injector when in the position shown in FIG. 6.
Figure 15:
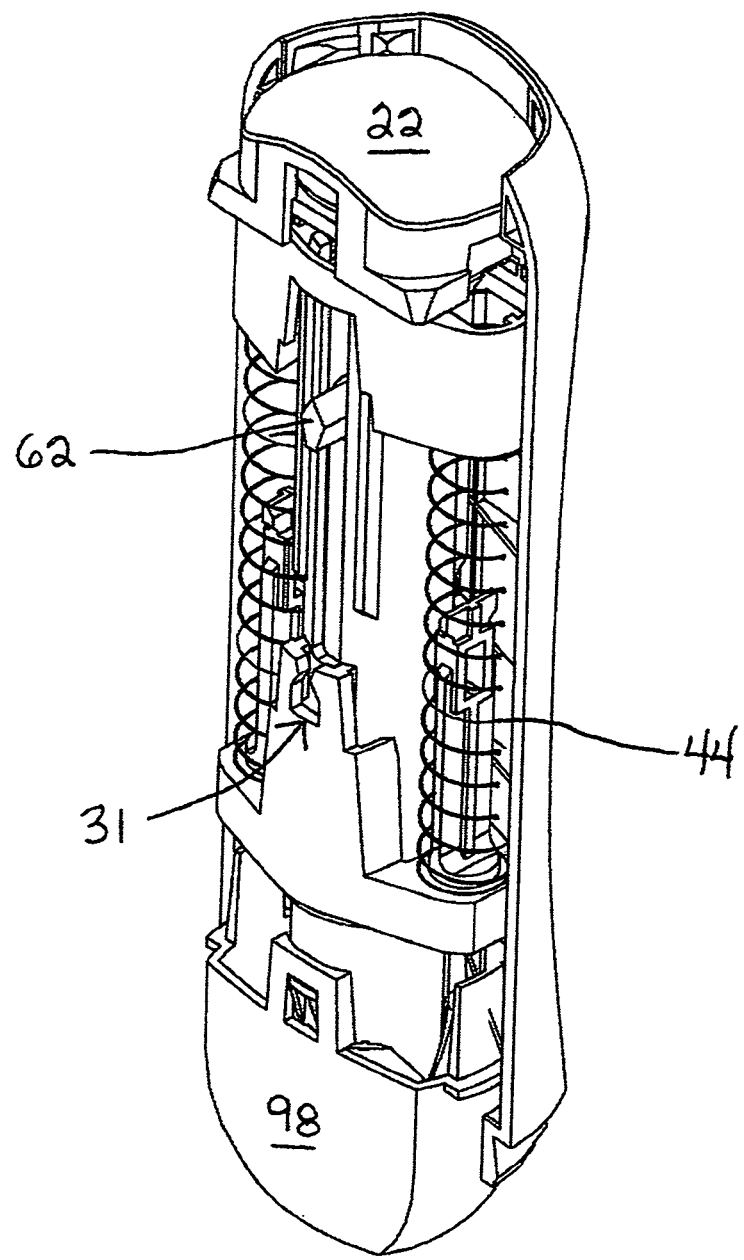
FIG. 15 is a perspective cutaway view of the auto-injector when in the position illustrated in FIG. 7.

In operation, in order to initiate activation, auto-injector 10 is pressed such that trigger 98 is against the body surface where the injection is to take place. Pressing of trigger 98 will cause actuating assembly 28 to move upwardly. This places actuating assembly 28 in a position wherein trigger 22 will be effective in activating the device. This position is illustrated in FIGS. 4 and 5 of the drawings. The patient will depress trigger 22 which will then release tabs 54 and 58 on legs 52 and 56 respectively. This permits springs 44 to drive plunger rod 60 against plunger 76. This results in first piercing tip 68 extending outwardly of the outer housing while also causing second piercing tip 70 to pierce pierceable top 80 of cartridge 74. The medicine is then injected into the patient.

Subsequently, after injection, spring 112 will cause upward movement of the needle hub 64 and cartridge 74 to thereby store the needle within the auto-injector.

Figure 16:
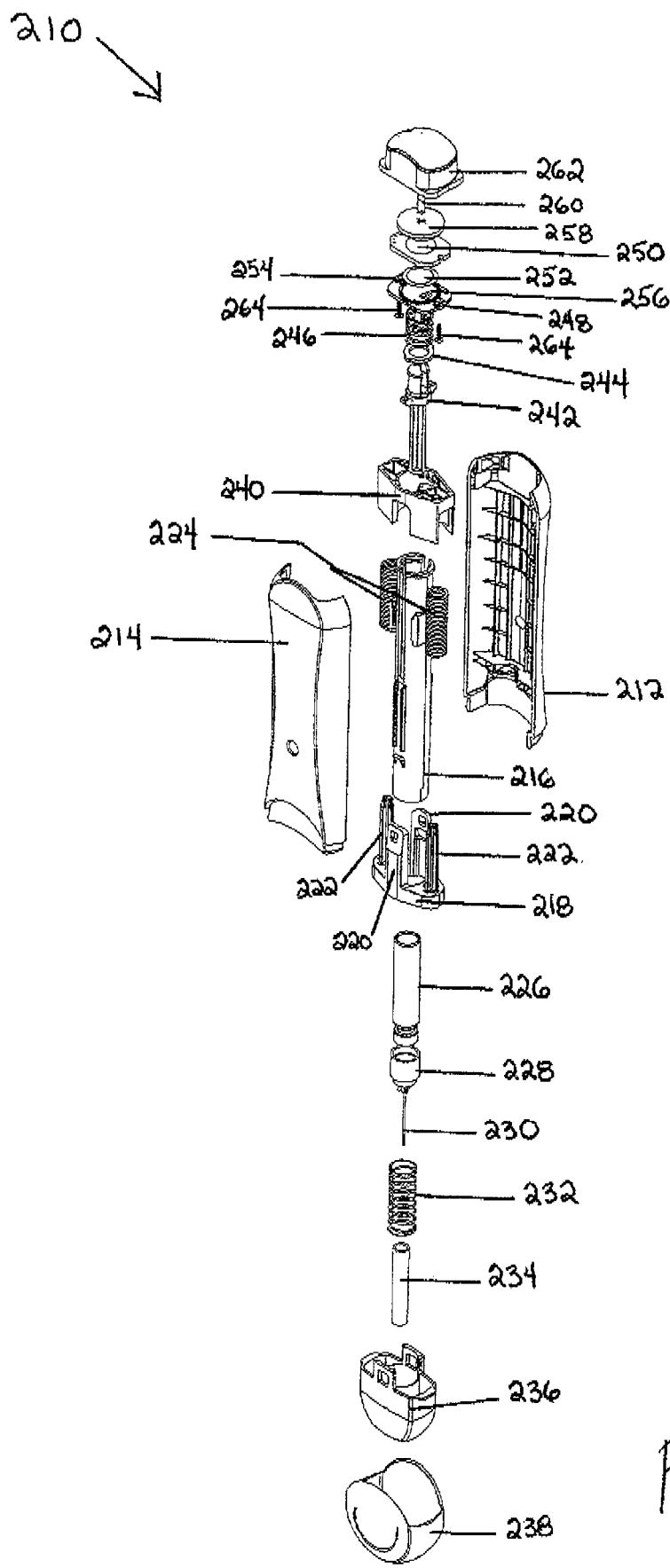
FIG. 16 is an exploded view of an auto-injector device according to an embodiment of the present invention.
Figure 17:
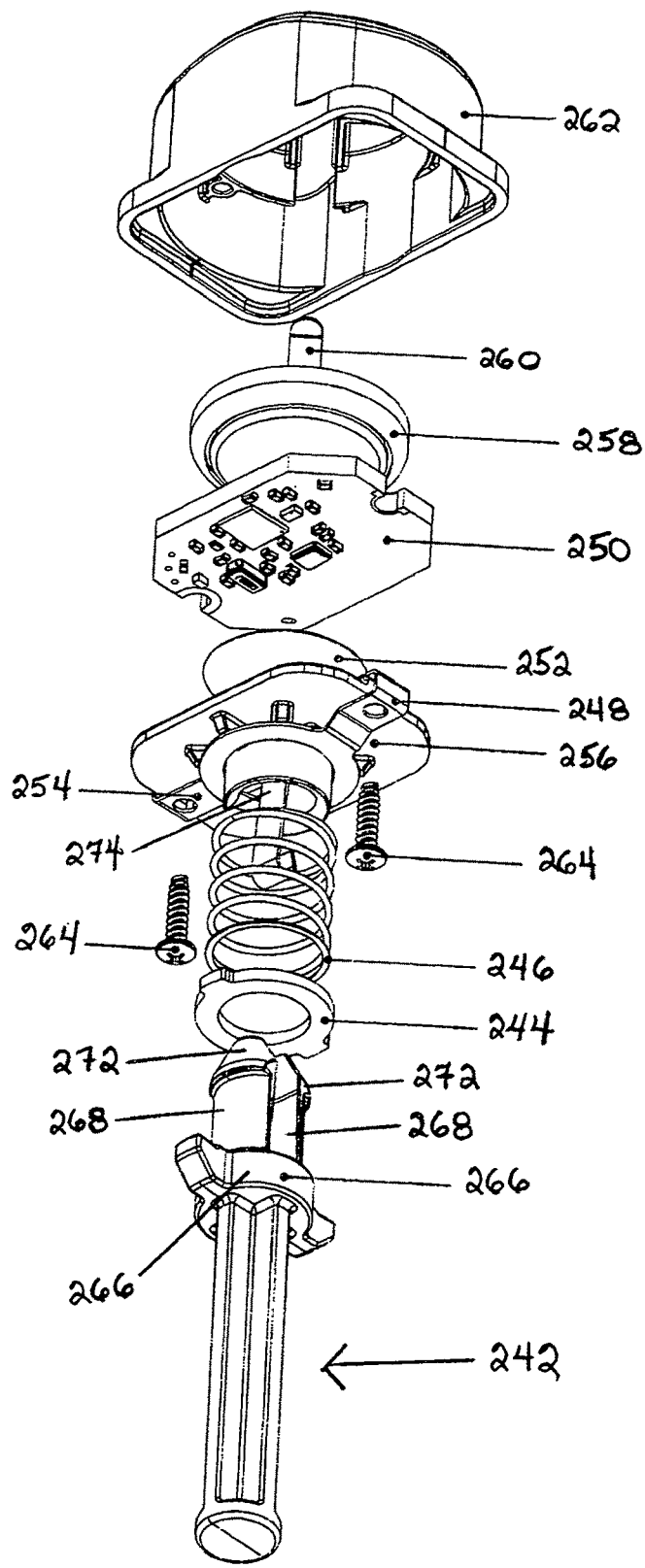
FIG. 17 is an exploded view of the upper end of the auto-injector device.
Figure 18:
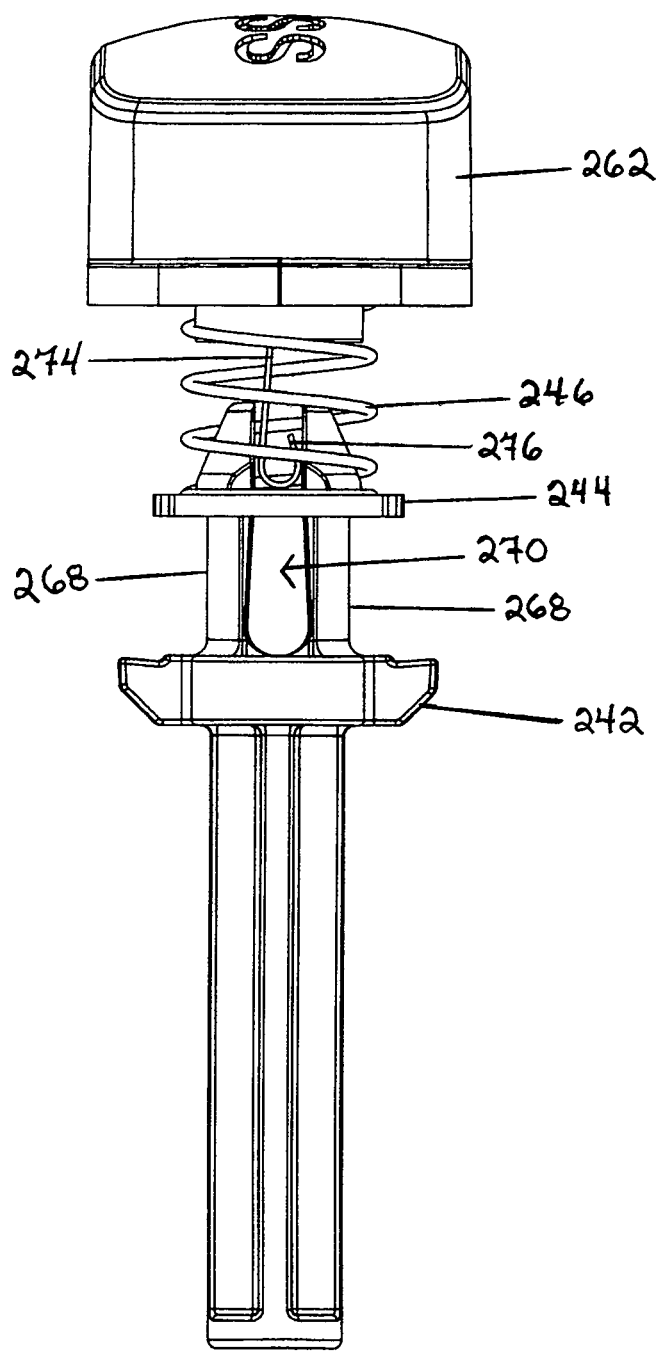
FIG. 18 is a side elevational view of the upper portion of the auto-injector device.
Figure 19:
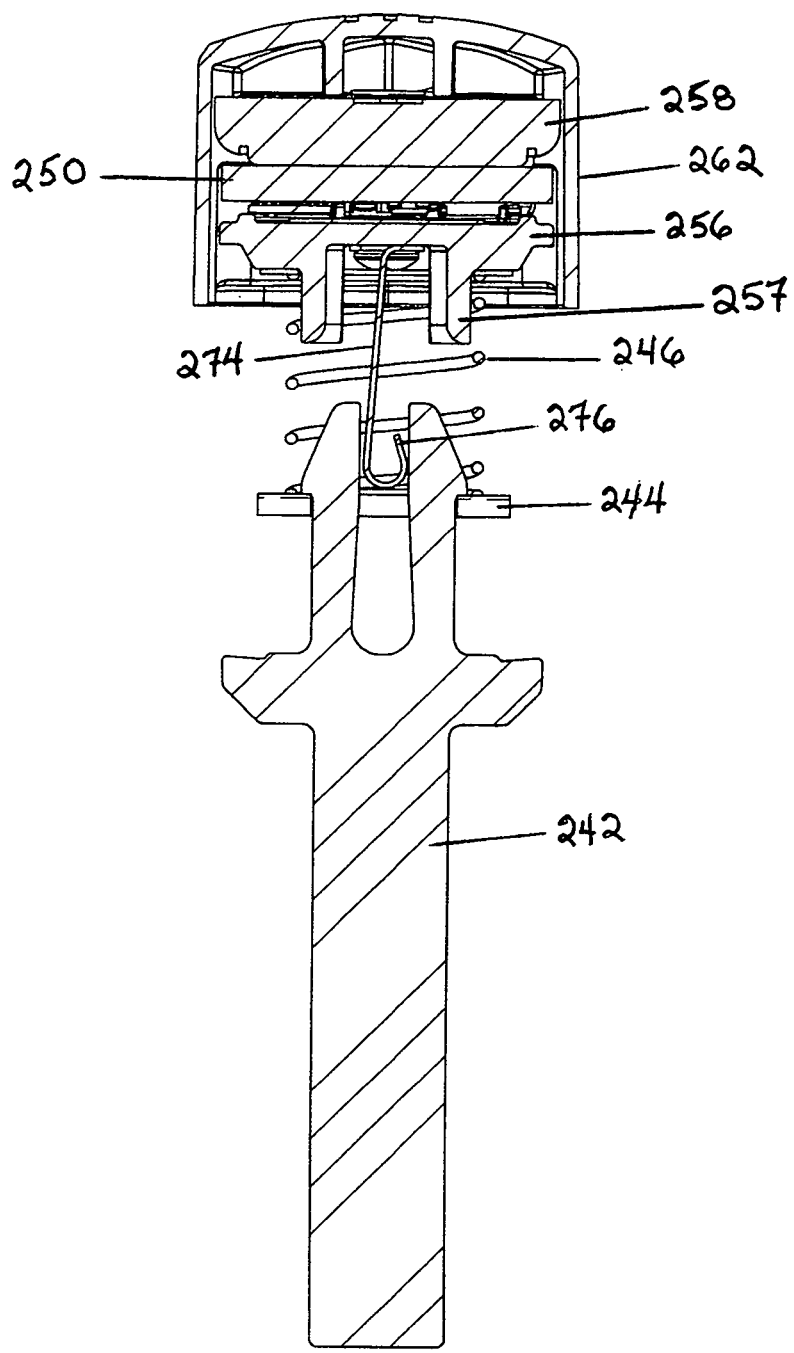
FIG. 19 is a cross sectional view thereof.
Figure 20:
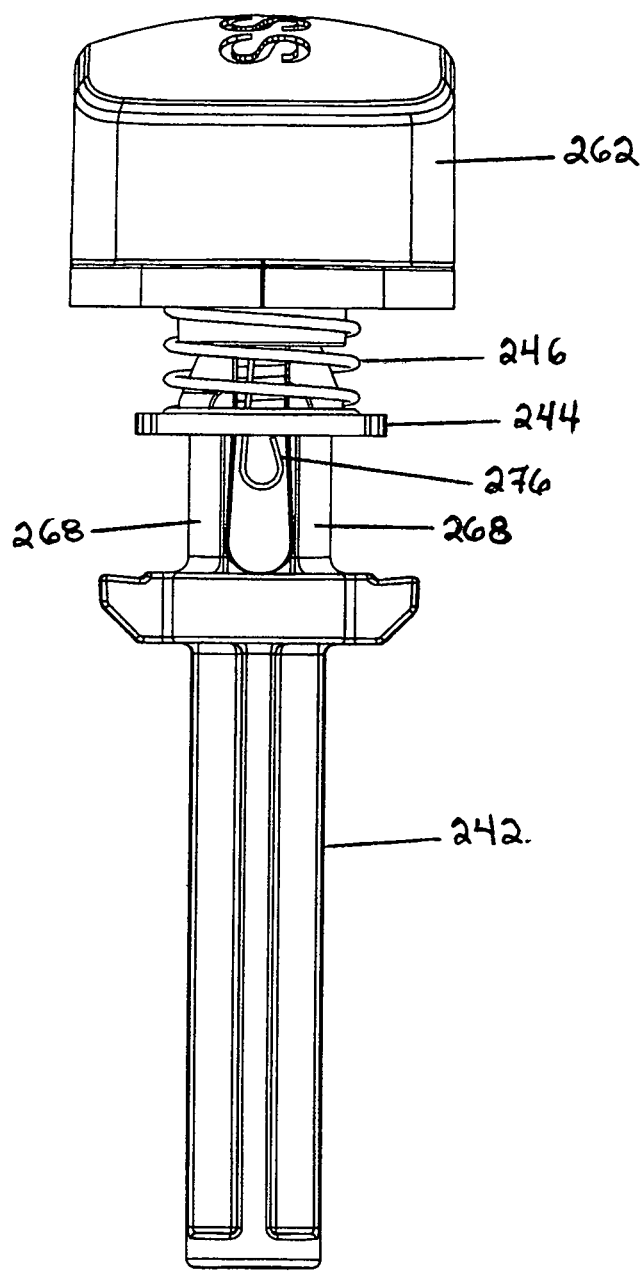
FIG. 20 is a side elevational view of the upper portion of the auto-injector device prior to activation.
Figure 21:
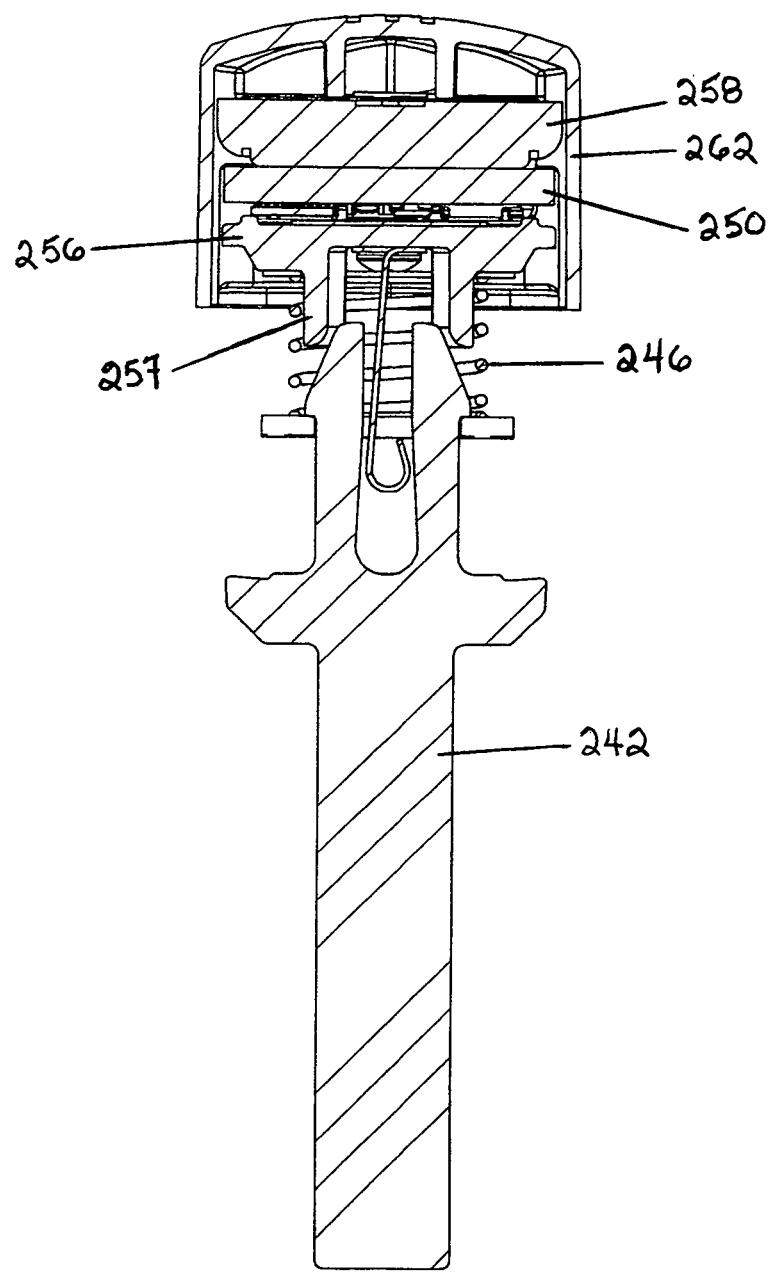
FIG. 21 is a cross sectional view thereof.
Figure 22:
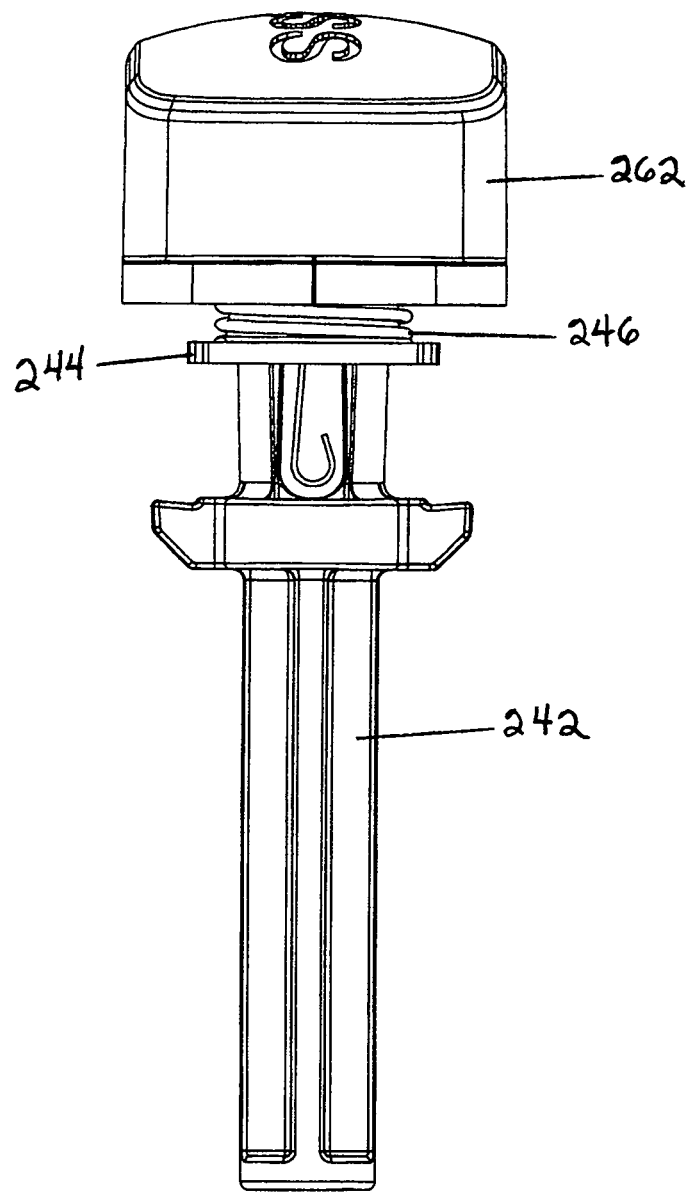
FIG. 22 is a side elevational view of the upper portion of the auto-injector prior to activation.

There is illustrated in FIG. 16 a further embodiment of an auto-injector which is generally designated by reference numeral 210.

Auto-injector 210 includes first and second outer housings 212 and 214 respectively. First and second outer housings may be secured together by conventional mechanical means (not shown).

Mounted interiorly of first outer housing 212 and second housing 214 is a sleeve 216. Sleeve 216 is associated with an actuator 218 which has a first pair of legs 220 which are mounted on opposed sides of actuator 218 and which are designed to engage with sleeve 216. A second set of legs 222 are also mounted on opposed ends and are arranged to receive coil injection springs 224.

Auto-injector 210 also includes a cartridge 226 which has a needle hub 228 attached thereto. A double ended needle 230 is mounted in needle hub 228. Auto-injection device 210 also includes a retraction spring 232 while about needle 230 there is provided a needle shield 234. At its end, auto-injector 210 is provided with a probe 236 and a removable cap 238 which fits over probe 236.

At the other end of housings 212, 214 there is provided a power cap 240. Included in the arrangement is a plunger rod 242 having a locking ring 244 mounted thereon. A coil spring 246 sits on top thereof and there is provided a positive contact 248 and a negative contact 254. The arrangement also includes a printed circuit board 250 which can be used for providing bluetooth capabilities. A speaker 252 is in electrical communication with printed circuit board 250. A battery 258 and battery holder 260 are provided. An activation button 262 is provided at the extremity. As shown in FIG. 16, screws 264 are utilized for retaining the sub-assembly in place with screws 264 engaging with threaded apertures 278 in activation button 262.

Referring back to plunger rod 242, it will be noted that there is provided an enlarged portion 266. Plunger rod 242 also has, at its upper end thereof, a pair of legs 268 which define therebetween an interior cavity 270. Each of legs 268 is provided with an enlarged end portion 272 in order that plunger rod 242 may be held in position. It will also be noted that PCB holder 256 has a downwardly extending portion 257 which is designed to engage enlarged portions 272 to force the same inwardly towards each other and thus permit release of the plunger rod when button 262 is pressed downwardly by the user.

Figure 23:
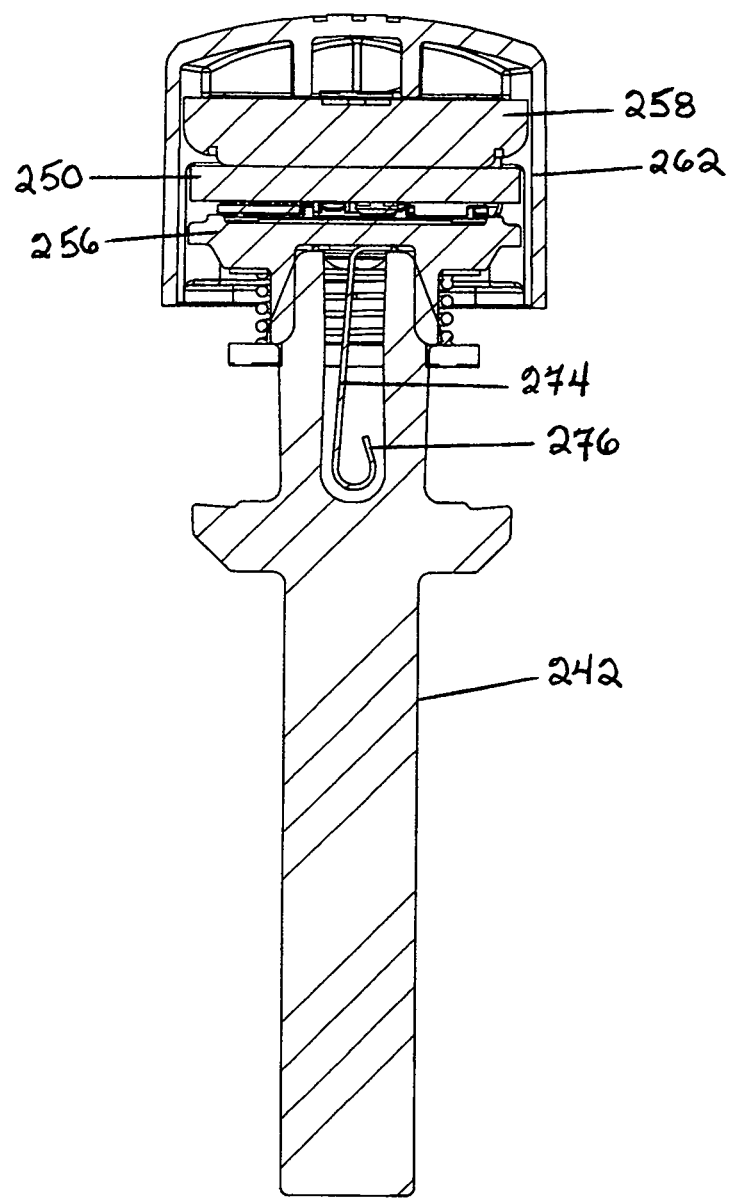
FIG. 23 is a cross-sectional view thereof.
Figure 24:
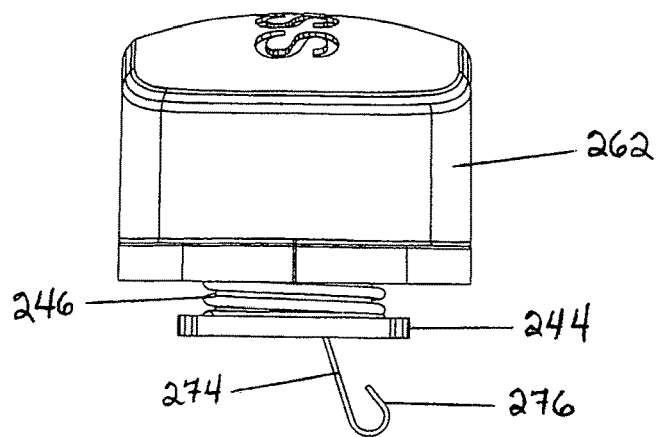
FIG. 24 is a side elevational view of the upper portion of the auto-injector after initial activation.
Figure 24:
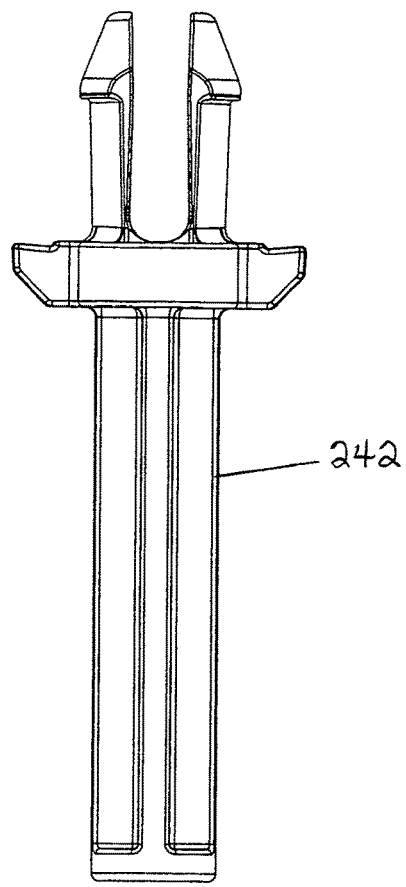
Figure 25:
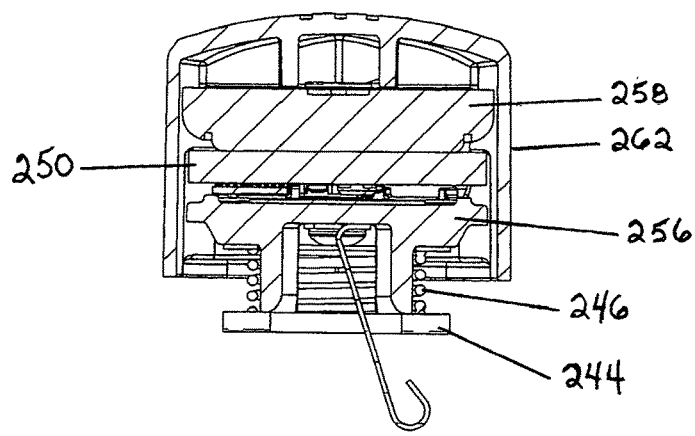
FIG. 25 is a cross-sectional view thereof.
Figure 25:
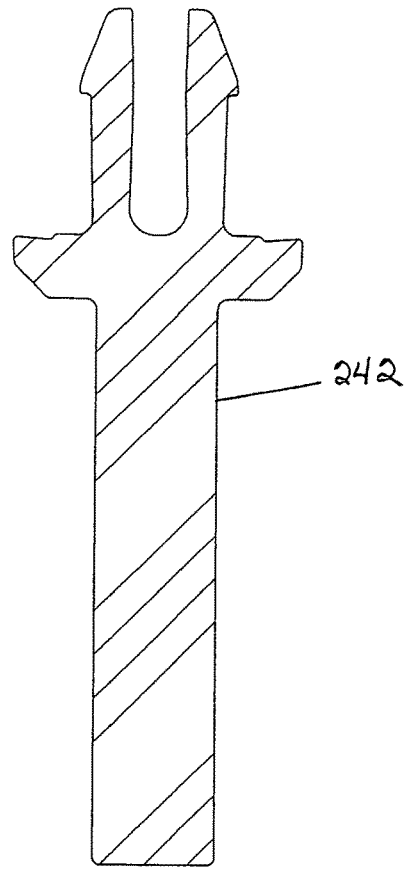
Figure 26:
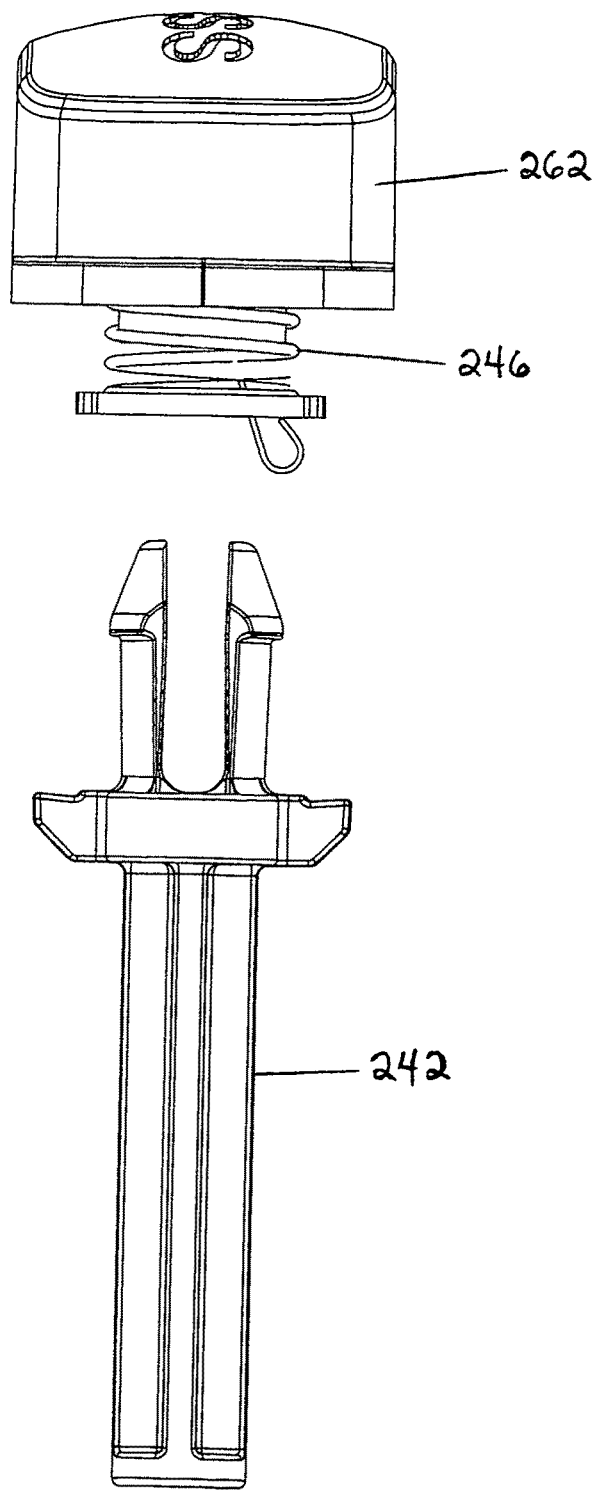
FIG. 26 is a side elevational view at the end of activation.
Figure 27:
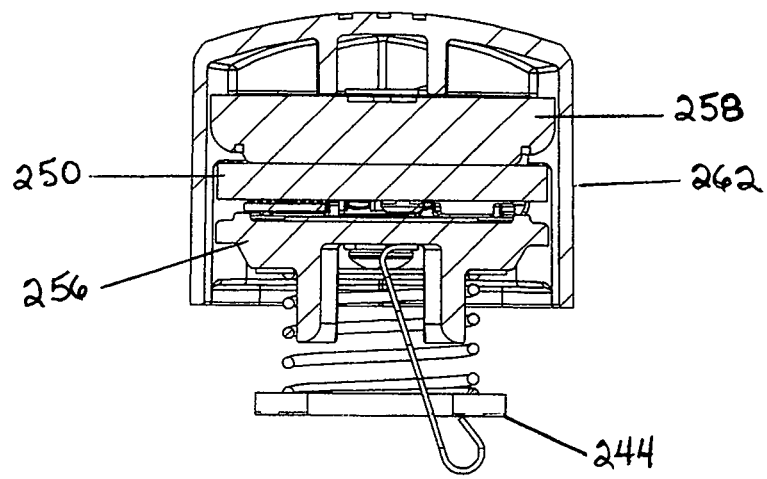
FIG. 27 is a cross-sectional view thereof.
Figure 27:
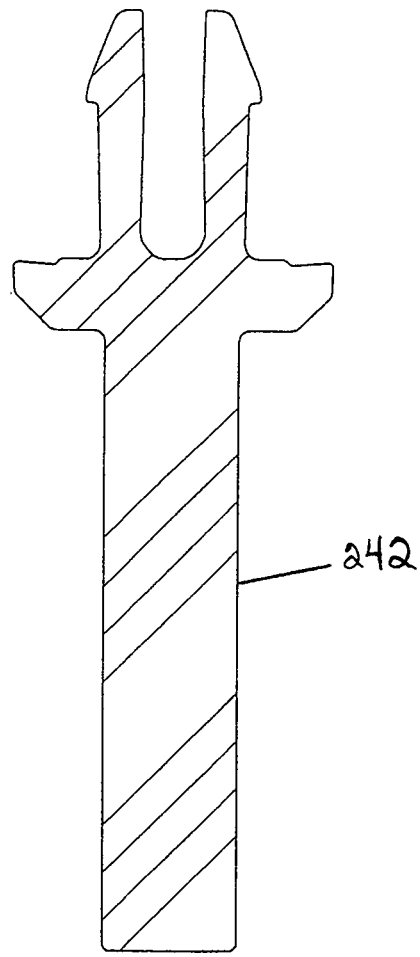

An electrically conductive member 274 is provided with a hook end 276. As seen in FIGS. 23 and 24, member 274 is biased to bend outwardly if not confined. Conductive member 274 is in contact with negative contact 254. Before activation, hook end 276 fits within interior cavity or recess 270 to prevent electrical communication.

As shown in the drawings, after activation, conductive member 274 is arranged such that hook end 276 will make contact with locking ring 244 via coil spring 246. There is an electrical communication with coil spring 246 and with negative contact 254. In turn, there is electrical communication with printed circuit board 250 and negative contact 254. This then completes the electric circuit and the printed circuit board is powered to perform the required tasks.

It will be understood that the above described embodiment is for purposes of illustration and that changes and modifications may be made thereto without departing from the spirit and scope of the invention.

We claim:

1. In an auto-injector device having a housing, a cartridge (226) for containing a medicament, a first needle tip (230) arranged to penetrate said cartridge, a second needle tip (230) for injecting said medicament into a target, said first and second needle tips (230) being in fluid communication, a plunger rod (242) to move said cartridge so as to be pierced by said first needle, said plunger rod having a recess (270) in an end thereof, the improvement comprising a battery (258), a printed circuit board (250) electrically communicating with said battery (258), an electrically conductive element (274) having a first end in electric communication with said battery (258) and printed circuit board (250), a second end (276) within said recess in said plunger rod, said second end (276) being electrically insulated, said electrically conductive element being biased outwardly, a coil spring (246) surrounding said electrically conductive element (274) and being spaced therefrom, the arrangement being such that when said plunger rod (242) is activated, said second end (276) of said electrically conductive element is released from said recess in said plunger rod and contacts said coil spring (246) to complete an electric circuit.

2. The improvement of claim 1 wherein said electrically conductive element is biased outwardly towards said coil spring.

3. The improvement of claim 2 wherein said electrically conductive element comprises a thin metallic strip.

4. An auto-injector (210) comprising:
an outer housing (212, 214) having a proximal end (18) and a distal end (16);
an inner housing (216), a cartridge (226) located within said inner housing (216), said cartridge (226) containing a medicament, said cartridge (226) having one end thereof sealed by a pierceable member;
a needle hub (228), said needle hub (228) having first and second piercing tips (230), said first and second piercing tips being in fluid communication;
a plunger rod (242) to move said cartridge so as to be pierced by said first piercing tip;
an actuating assembly (218), said actuating assembly (218) being arranged to move an actuator from a first storage position to an activated position wherein said first piercing tip (230) extends outwardly of said outer housing (212, 214) at said proximal end and said second piercing tip pierces said pierceable member;
a first trigger (262) being located at said distal end, a second trigger (236) being located at said proximal end, said first trigger (262) being spaced from said actuating assembly (218) such that depression of said first trigger (262) does not activate said actuating assembly, said second trigger (236), upon being activated, causes said actuating assembly (218) to move to then permit said first trigger to activate said actuating assembly; and a battery (258), a printed circuit board (250) electrically communicating with said battery, an electrically conductive element (274) having a first end in electric communication with said battery (258) and printed circuit board (250), a second end (276) within said recess (270) in said plunger rod (242), said second end being electrically insulated, said electrically conductive element being biased outwardly, a coil spring (246) surrounding said electrically conductive element and being spaced therefrom, the arrangement being such that when said plunger rod (242) is activated, said second end of said electrically conductive element is released from said recess in said plunger rod and contacts said coil spring (246) to complete an electric circuit.

* * * * *